(12) United States Patent
Frank

(10) Patent No.: US 6,794,371 B1
(45) Date of Patent: Sep. 21, 2004

(54) AMINOALKYLENEPHOSPHONATES FOR TREATMENT OF BONE DISORDERS

(75) Inventor: R. Keith Frank, Lake Jackson, TX (US)

(73) Assignee: The Dow Chemical Company, Midland, MI (US)

(*) Notice: Subject to any disclaimer, the term of this patent is extended or adjusted under 35 U.S.C. 154(b) by 91 days.

(21) Appl. No.: 10/088,884
(22) PCT Filed: Oct. 17, 2000
(86) PCT No.: PCT/US00/28713
§ 371 (c)(1), (2), (4) Date: Mar. 21, 2002
(87) PCT Pub. No.: WO01/28567
PCT Pub. Date: Apr. 26, 2001

Related U.S. Application Data
(60) Provisional application No. 60/160,019, filed on Oct. 18, 1999.

(51) Int. Cl.$^7$ ............. A61K 31/675; A61K 31/66; A61K 31/685
(52) U.S. Cl. ............. 514/80; 514/108; 514/76; 514/89
(58) Field of Search ............. 514/80, 108, 76, 514/89

(56) References Cited

U.S. PATENT DOCUMENTS

| | | | | |
|---|---|---|---|---|
| 3,288,846 A | * | 11/1966 | Irani et al. ............. 562/16 |
| 4,882,142 A | * | 11/1989 | Simon et al. ............. 424/1.77 |
| 4,898,724 A | * | 2/1990 | Simon et al. ............. 424/1.77 |
| 4,976,950 A | * | 12/1990 | Simon et al. ............. 424/1.77 |
| 5,385,893 A | * | 1/1995 | Kiefer ............. 424/9.363 |
| 5,714,604 A | * | 2/1998 | Kiefer ............. 540/472 |
| 5,902,825 A | * | 5/1999 | Jia ............. 514/492 |
| 6,008,207 A | * | 12/1999 | Brenner et al. ............. 514/108 |

FOREIGN PATENT DOCUMENTS

| | | | |
|---|---|---|---|
| EP | 0411941 A2 | * | 6/1991 |
| WO | WO 94/00145 | * | 1/1994 |

OTHER PUBLICATIONS

Miller et al., Toxicology and Applied Pharmacology, vol. 77, No. 2, 1985, pp. 230–239.*
Jee et al., Toxicology and Applied Pharmacology, vol. 92, No. 3, 1988, pp. 335–342.*
Moore et al., Fundamental and Applied Toxicology, (Apr. 1990) 14(3), 491–501.*
Wang et al., Shuichuli Jischu, abstract, 1989, 15(6), 370–3.*

* cited by examiner

Primary Examiner—Vickie Kim
Assistant Examiner—Brian-Yong S. Kwon
(74) Attorney, Agent, or Firm—Elisabeth T. Jozwiak

(57) ABSTRACT

A method for preventing loss of bone mineral in mammals which method comprises administering to a mammal an amount of an aminoalkylenephosphonate which is effective to prevent or minimize loss of bone material density. The aminoalkylenephophonates of the present invention should have at least one R-N(Alk-PO$_3$H$_2$)$_2$ group or at least two RRN-Alk-PO$_3$H$_2$ groups wherein R and R can be, same or different, aliphatic or cyclic moiety, and Alk is an alkylene group having from 1 to 4 carbon atoms.

2 Claims, No Drawings

AMINOALKYLENEPHOSPHONATES FOR TREATMENT OF BONE DISORDERS

This application claims the benefit of provisional application Ser. No. 60/160,019, filed Oct. 18, 1999.

This invention relates to the use of aminoalkylenephosphonates for treatment of bone disorders such as osteoporosis.

This invention involves the use of aminoalkylenephosphonates, such as, for example, 1,4,7,10-tetraazacyclododecane-1,4,7,10-tetramethylenephosphonic acid (DOTMP) and 3,6,9,15-tetraazabicyclo[9.3.1]tetradeca1(15),11,13-triene-3,6,9-trimethylenephosphonic acid (PCTMP) for use in the inhibition of bone resorption. This application is directed toward use in the prevention and/or treatment of bone diseases such as osteoporosis. Bone is a dynamic tissue, continually undergoing remodeling. Hydroxyapatite, the main inorganic constituent of bone, is constantly being deposited and resorbed. In pathological states such as osteoporosis a shift in the balance of these two processes occurs, resulting in a net loss of mineralized tissue. This loss results in impaired skeletal function and clinical fractures. Osteoporosis is an enormous public health problem affecting as many as 25 million people in the United States alone. It is a pervasive disease that has staggering costs to society in terms of morbidity, mortality, and economics. As the population becomes more aged, the magnitude of this problem will certainly become greater.

Currently only three drugs—estrogen, calcitonin, and alendronate are approved by the FDA for use in the treatment of osteoporosis. Both estrogen and calcitonin have some drawbacks (for example, estrogen—risk of endometrial carcinoma, calcitonin—allergic reaction) and are not always successful. The recently approved bisphosphonate alendronate (4-amino-1-hydroxybutylidenebisphosphonate) is a member of a class of compounds that has received much attention for their potential in treating bone-related illnesses.

Bisphosphonates all contain the basic P-C-P structure. Examples such as etidronate (1-hydroxyethylidenebisphosphonate), risedronate [1-hydroxy-2-(3-pyridinyl)ethylenebisphosphonate], pamidronate (3-amino-1-hydroxypropylidenebisphosphonate), tiludronate (4-chlorophenylthiomethylenebisphosphonate) have already been approved for the treatment of a rare bone condition called Paget's disease.

Aminoalkylenephosphonates have not been investigated for these applications. It is known that these compounds have a strong affinity for bone (for example, EDTMP and DOTMP radiopharmaceutical bone agents) and have low soft tissue localization. They have unique properties such as the ability to inhibit calcium phosphate scale formation at very low concentrations.

It has now been discovered that aminoalkylenephosphonates can inhibit bone mineral density loss. In fact, a screening study of various aminomethylenephosphonates in an ovarectomized rat osteoporosis model has now shown that PCTMP is as good as, and may even be superior to, alendronate in its ability to inhibit bone mineral loss.

The present invention relates to a method for preventing or minimizing loss of bone mineral in mammals which method comprises administering to a mammal an amount of an aminoalkylenephosphonate which is effective to prevent or minimize loss of bone mineral density.

In another aspect, the present invention relates to the use of an aminoalkylenephophonate or a pharmaceutically acceptable salt thereof in the manufacture of a pharmaceutical formulation for preventing or minimizing loss of bone mineral in mammals.

The term "aminoalkylenephosphonate" as used herein refers to those phosphonates and phosphonic acids which incorporate an amine moiety, whether aliphatic or cyclic, attached via the amine nitrogen through an alkylene group to the phosphonate or phosphonic acid moiety. The aminoalkylenephosphonates of the present invention should have at least one R-N(Alk-PO$_3$H$_2$)$_2$ group or at least two RR' N-Alk-PO$_3$H$_2$ groups wherein R and R' can be, same or different, aliphatic or cyclic moiety, and Alk is an alkylene group having from 1 to 4 carbon atoms.

The amine moiety of the aminoalkylenephosphonates of the present invention represented by the R-N= and RR' N— in the aforementioned R-N(Alk-PO$_3$H$_2$)$_2$ and RR' N-Alk-PO$_3$H$_2$ groups is derived from either an aliphatic or a cyclic polyamine in which hydrogen atoms bonded to the nitrogen atom(s) in the amine moiety are partially or completely substituted by an alkylphoshonate group. Non-limiting examples of the amines suitable as amine moieties in the practice of the present invention are ethylenediamine (EDA), diethylenetriamine (DETA), triethylenetetraamine (TETA), 1,4,7,10-tetraazacyclododecane, 3,6,9,15-tetraazabicyclo [9.3.1]tetradeca-1(15),11,13-triene, 2,11-diaza[3.3](2,6)pyridinophane, 2-(aminomethyl)pyridine, 2,6-bis(aminomethyl)pyridine.

The alkylene group having from 1 to 4 carbon atoms contemplated by Alk in the aforementioned formulas can be straight or branched chain alkylene group. Non-limiting examples of such alkylene groups are methylene, ethylene, propylene, isopropylene, and butylene. The preferred alkylene group is methylene (—CH$_2$—) group.

Preferred aminoalkylenephosphonates are aminomethylenephosphonates. Particularly preferred aminoalkylenephosphonates are 1,4,7,10-tetraazacyclododecane-1,4,7,10-tetramethylenephosphonic acid (DOTMP), 3,6,9,15-tetraazabicyclo[9.3.1]tetradeca-1(15),11,13-triene-3,6,9-trimethylenephosphonic acid (PCTMP), N,N'-bis(methylenephosphonic acid)-2,11-diaza[3.3](2,6)pyridinophane (BP2MP) and N,N-bis(methylene phosphonic acid)-2-(aminomethyl)pyridine (AMPDMP).

The aminoalkylenephosphonates contemplated by the present invention are well known in the art and numerous methods for their preparation have been disclosed. See, for example, U.S. Pat. No. 3,288,846 (Irani et al) and U.S. Pat. No. 4,898,724 (Simon et al), both incorporated herein by reference.

The aminoalkylenephosphonates of the present invention are used in an amount effective to prevent or minimize loss of bone mineral. The effective amount will vary depending on the mammal, aminoalkylenephosphonate used and the method of its administration (for example, oral or parenteral). A person of ordinary skill in the art will know how to determine the effective amount of aminoalkylenephosphonate.

The aminoalkylenephosphonates of the present invention can be administered to a mammal on a daily or weekly regiment basis. Typically, for average 50 kg mammal, the effective weekly parenteral dose is in the range of from about 0.01 mg to about 500 mg, preferably from about 0.1 mg to about 250 mg, most preferably from about 0.1 to about 70 mg. Typically, for average 50 kg mammal, the effective daily oral dose is in the range of from about 0.1 mg to about 40 g, preferably from about 0.1 mg to about 10 g, most preferably from about 0.1 to about 5 g.

In the practice of the present invention the aminoalkylenephosphonate may be administered per se or as a component of a pharmaceutically acceptable composition.

Thus, the present invention may be practiced with the aminoalkylenephosphonate being provided in pharmaceutical formulation, both for veterinary and for human medical use. Such pharmaceutical formulations comprise the active agent (the aminoalkylenephosphonate) together with one or more pharmaceutically acceptable carriers thereof and optionally any other therapeutic ingredients. The carrier(s) must be pharmaceutically acceptable in the sense of being compatible with the other ingredients) in the formulation and not unsuitably deleterious to the recipient thereof. The aminoalkylenephosphonate is provided in an effective amount, as described above, and in a quantity appropriate to achieve the desired dose.

The formulations include those suitable for oral, rectal, topical, nasal, ophthalmic, or parenteral (including subcutaneous, intramuscular, and intravenous) administration. Formulations may be prepared by any methods well known in the art of pharmacy. Such methods include the step of bringing the aminoalkylenephosphonate into association with a carrier, which constitute one or more accessory ingredients. In general, the formulation may be prepared by uniformly and intimately bringing the aminoalkylenephosphonate into association with a liquid carrier, a finely divided solid carrier, or both, and then, if necessary, shaping the product into desired formulation. In addition, the formulations of this invention may further include one or more accessory ingredient(s) selected from diluents, buffers, flavoring agents, binders, disintegrants, surface active agents, thickeners, lubricants, preservatives.

The following Examples are provided to illustrate the present invention, and should not be construed as limiting thereof.

Example 1

Eleven week old Female Sprague-Dawley laboratory rats (75) were fed a commercial rat diet and were allowed to drink water ad libitum. They were housed in pairs in an air-conditioned environment, and were allowed to enjoy 14 hours of illumination per day. Ten rats were sham-operated and were used as "non-osteopenic" control rats. All of the other rats were ovariectomized at 12 weeks of age. All surgeries were done under injectable anesthesia. Ten of the ovariectomized rats were used as an "osteopenic but non-treated" control, and did not receive any phosphonate treatments. The remaining rats were given various phosphonate compounds in groups of ten.

Phosphonates (5 mg/kg) were administered subcutaneously (to insure better bioavailability). The rats were given doses three times during the first week and once a week thereafter.

Structures of the compounds tested are shown below in Figure 1.

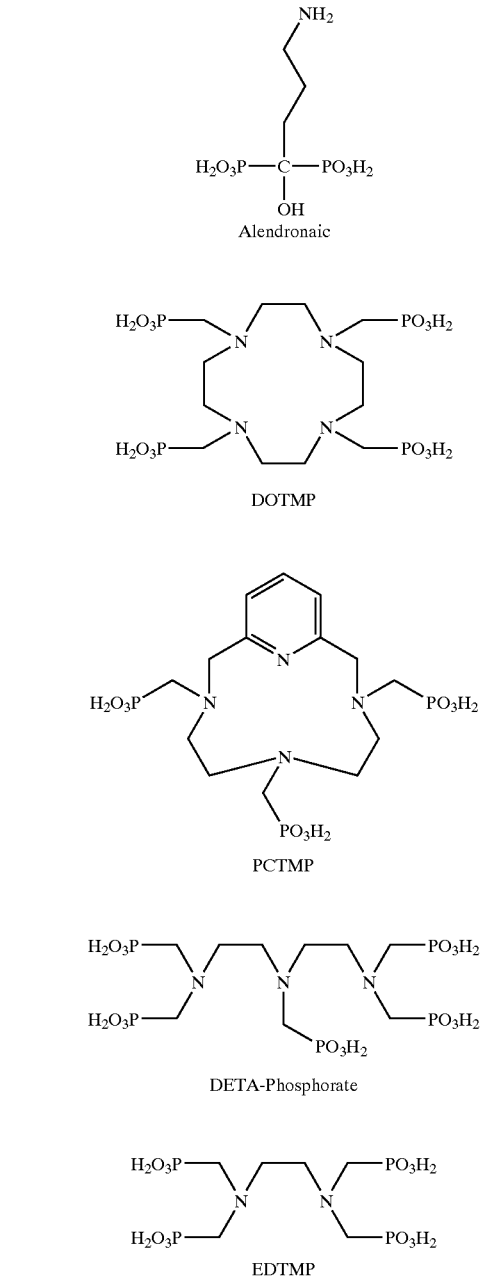

Figure 1. Structures of Compounds Tested (Example 1)

Bone mineral density was determined by single photon absorptiometry while the rats were under injectable anesthesia. The distal femoral metaphysis of all rats were scanned at weekly intervals for ten weeks.

Figure 2 below shows the average drop in bone mineral density, normalized to the sham-operated control group, for the ovariectomized (OVX) control group and for the treatment groups.

FIG. 2
Average Change in BMD
(Normalized to sham-operated control = 0)

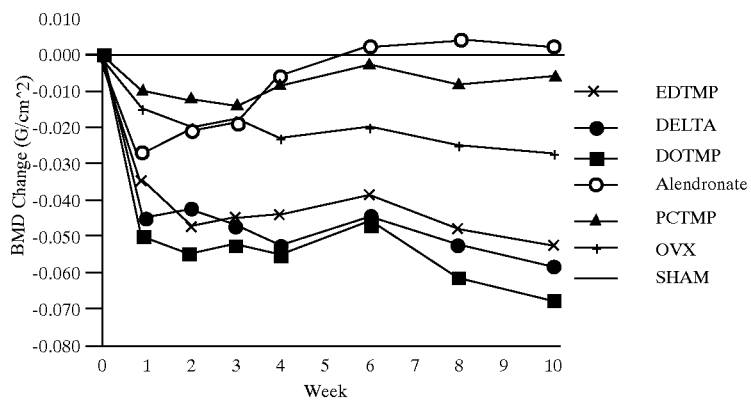

As can be seen, relative to the sham-operated control, the OVX group loses bone mineral density (BMD) over time. Three aminomethylenephosphonates, DOTMP, EDTMP, and DETA-Phosphonate, all lost more BMD than the OVX group (at this dose level). Both the alendronate and PCTMP groups maintained BMD. (Because of the difference in molecular weight, PCTMP was actually used at a lower dose level than alendronate on a mole basis.)

By week 10, there are three statistical groupings. The sham operated controls, alendronate, and PCTMP are all statistically equivalent. The ovariectomized controls are in a group by themselves, as are the other three aminomethylenephosphonates.

Example 2

A second study was undertaken to explore the effect of structural changes in PCTMP. The structures of the compounds tested are shown below in Figure 3. Included in the study was DOTMP at one tenth the dose, that is, 0.5 mg/kg. All other compounds were dosed at 5 mg/kg. In this study, bone mineral density was determined by dual energy X-ray absorptiometry (DEXA). Other aspects of the study were substantially the same as in Example 1. The results of the study are shown in Figure 4 below.

Again, it can be seen that, relative to the sham-operated controls, the OVX control group lost significant BMD over the study period. As before, PCTMP shows an improvement over the OVX group. AMPDMP and BP2MP both look even better, but the best compound tested was DOTMP at 0.5 mg/kg. At this dose level it was equivalent to the sham-operated control.

Figure 3. Structures of Compounds Tested

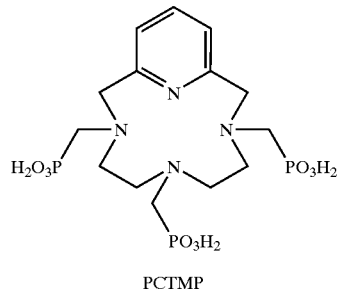

PCTMP

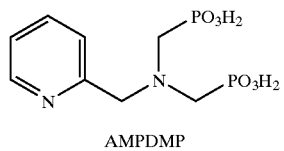

AMPDMP

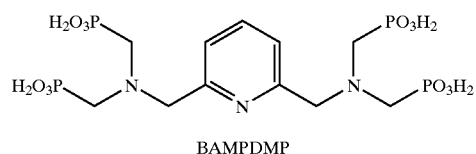

BAMPDMP

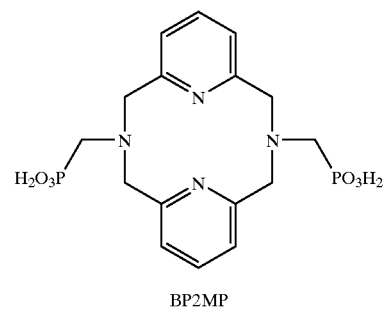

BP2MP

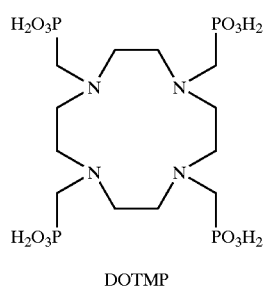

DOTMP

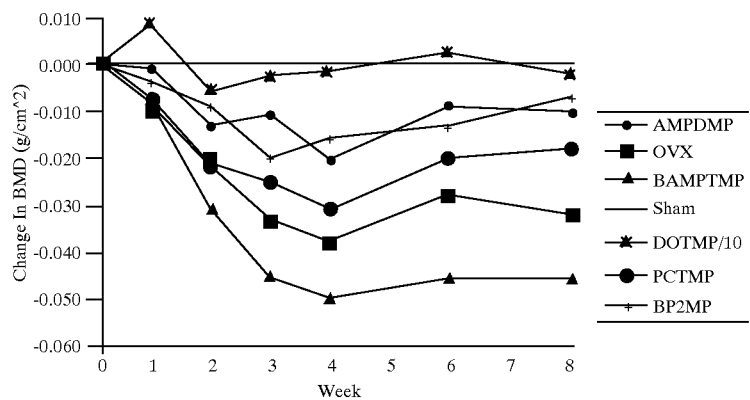

FIG. 4
Average Change in BMD
(Normalized to sham-operated control = 0)

What is claimed is:

1. A method for minimizing loss of bone mineral in mammals which method comprises administering to a mammal an amount of an aminoalkylenephosphonate or a pharmaceutically acceptable salt thereof which is effective to minimize loss of bone mineral density, wherein the aminoalkylenephosphonate is selected from the group consisting of 3,6,9,15-tetraazabicyclo[9.3.1]tetradeca-1(15),11,13-triene-3,6,9-trimethylenephosphonic acid (PCTMP), N,N'-bis(methylenephosphonic acid)-2,11-diaza[3.3](2,6)pyridinophane (BP2NO), and N,N'-bis(methylenephosphonic acid)-2-(aminomethyl)pyridine (AMPDMP).

2. A method for minimizing loss of bone mineral in mammals which method comprises administering to a mammal a pharmaceutical formulation consisting essentially of an amount of aminoalkylenephosphonate or a pharmaceutically acceptable salt which is effective to minimize loss of bone mineral density, wherein said aminoalkylenephosphonate is 1,4,7,10-tetraazacyclododecane-1,4,7,10-tetramethylenphosphonic acid (DOTMP).

* * * * *